(12) United States Patent
Rao

(10) Patent No.: US 6,218,587 B1
(45) Date of Patent: Apr. 17, 2001

(54) CATALYTIC HYDROGENOLYSIS

(75) Inventor: V. N. Mallikarjuna Rao, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 08/313,941

(22) Filed: Sep. 27, 1994

Related U.S. Application Data

(63) Continuation of application No. 07/633,922, filed on Dec. 26, 1990, now abandoned.

(51) Int. Cl.$^7$ .................................................. C07C 17/10
(52) U.S. Cl. ............................................................ 570/176
(58) Field of Search .............................................. 570/176

(56) References Cited

U.S. PATENT DOCUMENTS

| | | | | |
|---|---|---|---|---|
| 2,942,036 | * | 6/1960 | Smith | 570/176 |
| 3,439,052 | * | 4/1969 | Bjornson | 570/176 |
| 5,053,564 | * | 10/1991 | Cheminal | 570/176 |

FOREIGN PATENT DOCUMENTS

| | | | | |
|---|---|---|---|---|
| 593529 | * | 3/1960 | (CA) | 570/176 |
| 593 529 | | 3/1960 | (CA) | 570/176 |
| 3619079 | * | 12/1986 | (DE) | 570/176 |
| 0 347 830 | | 12/1989 | (EP) | C07C/19/08 |
| 0347830 | * | 12/1989 | (EP) | 570/176 |
| 1578933 | * | 1/1980 | (GB) | 570/176 |
| 1 578 933 | | 11/1980 | (GB) | C07C/19/08 |
| 1578933 | | 11/1980 | (GB) . | |
| 1128942 | | 2/1989 | (JP) . | |
| 1-128942 | | 5/1989 | (JP) | C07C/19/08 |
| WO 90/08748 | | 8/1990 | (WO) . | |
| 9008753 | * | 10/1990 | (WO) | 570/176 |

OTHER PUBLICATIONS

Robert L. Augustine, *Catalytic Hydrogenation*, 1965, Marcel Dekker, Inc., p. 38.
Paul N. Rylander, *Catalytic Hydrogenation over Platinum Metals*, 1967, Academic Pres, p. 19.
James T. Richardson, *Principles of Catalyst Development*, 1989, Plenum Press, p. 206.
A.A. Goleva, et al. *Catalytic Dehydrochlorination of Chloroethanes II Catalytic Dehydrochlorination of 1,1,2,2–Tetrachloroethane*, Russian Journal of Physical Chemistry, 44(1970), pp. 290–291.
Biswas, et al., Vinyl Polymerization by Carbon Black II, Modification of Carbon Black and its use in the Polymerization of N. Vinylcarbazole, Sci–Chem, (1983), pp. 861–876 A. 20.
Horning, et al., *Organic Synthesis Palladium Catalysts*, John Wiley & Sons Inc, Collective vol. 3, 1955, pp. 685–690.

John W. Hassler, *Activated Carbon*, Chemical Publishing Co. Inc., 1963, pp. 344–345.
Smisek, et al., *Active Carbon*, Elsevier Publishing Co., 1970, pp. 61–70.
F.J. Long et al., *The Effect of Specific Catalysts on the Reactions of the Steam Carbon System*, Proc. Roy. Soc., (London) A215, pp. 100–110, (1952).
A. Blackburn et al., *Absorption from Binary Liquid Mixtures*: Some effects of ash in commercial charcoal J. Chem. Soc. 4103 (1955) pp.4103–4106.
F. J. Long et al., *The Catalysis of the Oxidation of Carbon*, J. Chim. Phys., 47, 1950, pp. 361–378.
R.B. Anderson et al. *Surface Complexes of Charcoal*, J. Phys. Colloid, Chem, 51, 1947, pp. 1308–1329.
H. M. Fray, *A New Type of Catalytic Effect in the Oxidation of Carbon*, Proc. Roy Soc. (London) A 228, 1955, pp. 510–518.
Augustine, R.L., "Catalysts and Conditions", *Catalytic Hydrogenation*, Marcel Dekker, Inc., p. 38 (1965).
Rylander, P.N., "Inhibitors and Poisons", *Catalytic Hydrogenation Over Platinum Metals*, Academic Press, p. 19 (1967).
Richardson, J.T., "Catalyst Deactivation", *Principles of Catalyst Development*, Plenum Press, pp. 205–207 (1989).
Goleva, A.A. et al, "Catalytic Dehydrochlorination of Chloroethanes. II. Catalytic Dehydrochlorination of 1,1,2,2–Tetrachlorethane", *Russian Journal of Phys. Chemistry*, 44(2), pp. 290–291 (1970).
Biswas, M. et al, "Vinyl Polymerization by Carbon Black. II. Modification of Carbon Black and Its Use in the Polymerization of N–Vinylcarbazole", *J. Macromol. Sci.–Chem.*, A20(8), pp.861–876 (1983).
Chemical Abstracts: Aliphatics, 80, Abstract Nos. 145469w and 145470q (1974).
Smisek, M. et al, *Active Carbon*, Elsevier Publishing Company, pp. 61–70 (1970).
Long, F.J. et al, "The Effect of Specific Catalysts on the Reactions of the Steam–Carbon System", *Proc. Roy. Soc (London)*, A215, pp. 100–110 (1952).
Blackburn, A. et al, "Adsorption from Binary Liquid Mixtures", *J. Chem. Soc.*, pp. 4103–4106 (1955).
Horning, E.C. et al (Eds.), "Palladium Catalysts", *Organic Synthesis*, John Wiley, 3, pp. 685–690 (1963).
Hassler, J.W. *Activated Carbon*, Chemical Publishing Co., pp.343–345 (1963).
Long, F.J., et al, "The Catalysis of the Oxidation of Carbon", *J. Chim. Phys.*, 47, pp. 361–378 (1950).
Anderson, R.B et al, "Surface Complexes on Charcoal", *J. Phys. Colloid. Chem.*, 51, pp. 1308–1329 (1947).

(List continued on next page.)

Primary Examiner—Alan Siegel

(57) ABSTRACT

Catalytic hydrogenolysis of fluorohalocarbons (e.g., CFCs) and fluorohalohydrocarbons (e.g., HCFCs), using low-phosphorous, low-sulfur catalysts of Re, Co, Ni, Ru, Rh, Pd, Os, Ir, and/or Pt on carbon. Preferred catalysts are acid-washed and also have a low content of potassium, sodium and iron.

20 Claims, No Drawings

OTHER PUBLICATIONS

Frey, H.M., "A New type of Catalytic Effect in the Oxidation of Carbon", *Proc. Roy. Soc.* (London), A228, pp. 510–518 (1955).

*Chemical Abstracts*, vol. 112, Abstract No. 216213a (1990).

*Chemical Abstracts*, 111, Abstract No. 114734h (1989).

*Ullmann's Encyclopedia of Industrial Chemistry*,(5th Ed.), A5, pp. 130–135 (1986).

Gates et al, *Chemistry of Catalytic Processes*, pp. xi, and 248–249 (1979).

Goleva, A.A., "Catalytic Dehydrochlorination of Chlorinated Ethanes I. Catalytic Dehydrochlorination of 1,2–Dichloroethane", *Russian Journal of Phys. Chem.*, 44(1), pp. 137–139 (1970).

Hickok, R. L., A Study of the Catalytic Hydrogenation of Some Polyhalo Derivatives of Methane and Ethane, 20–21, 1958.

Chemical Abstracts, 10–Organic Chemistry, 15417, (1958).

Dissertation Abstr. (18), 1640, (1958).

* cited by examiner

CATALYTIC HYDROGENOLYSIS

This is a continuation of application Ser. No. 07/633,922 filed Dec. 26, 1990, now abandoned.

BACKGROUND OF THE INVENTION

1. Field of the Invention

This invention relates to the catalytic hydrogenolysis of fluorohalocarbons or fluorohalohydrocarbons and more particularly to carbon supported Group VII or Group VIII metal catalysts and their use in the hydrogenolysis of fluorohalocarbons or fluorohalohydrocarbons.

2. Background

A number of chlorinated fluorocarbons are considered to be detrimental toward the Earth's ozone layer. There is a world-wide effort to develop materials that can serve as effective replacements. For example, 1,1,1,2-tetrafluoroethane (HFC-134a), a fluorohydrocarbon containing no chlorine, is being considered as a replacement for dichlorodifluoromethane (CFC-12) in refrigeration systems because of its zero ozone depletion potential. There is thus a need for manufacturing processes that provide fluorocarbons that contain less chlorine.

One method of reducing the chlorine content of halogen substituted hydrocarbons containing chlorine as well as fluorine is reacting organic starting materials containing chlorine and fluorine with hydrogen at elevated temperature in the presence of a hydrogenation catalyst. (e.g. supported Group VII or Group VIII metal catalysts). British Patent Specification 1,578,933 discloses, for example, that HFC-134a can be prepared by the hydrogenolysis of 2,2-dichloro-1,1,1,2-tetrafluoroethane (CFC-114a) or 1,1,1,2-tetrafluorochloroethane (HCFC-124) over palladium on carbon or palladium on alumina hydrogenation catalysts. There remains a continued interest in providing improved hydrogenolysis processes for the manufacture of HFC-134a as well as other fluorohydrocarbons and fluorohalohydrocarbons.

Techniques for enhancing the activity of Group VIII metal hydrogenolysis catalysts have been disclosed. The catalyst improvements described in Eur. Pat. Appln. 347,830 and Jap. Pat. Appln. 1-128,942 are achieved by the addition of other elements, such as Group IB, lanthanum, lanthanide elements, and rhenium to the Group VIII metal catalysts. The additives are said to prevent sintering and also increase the activity and the mechanical strength of the catalysts.

Palladium catalysts are considered generally to be resistant to catalyst poisons (Augustine, "Catalytic Hydrogenation" Marcel Dekker, inc., N.Y., 1965, page 38); although Rylander "Catalytic Hydrogenation over Platinum Metals," Academic Press, New York, 1967, p. 19, reveals that all types of metal cations may cause drastic inhibition of platinum metal catalysts. However, there is no way of generalizing what the effect of any particular cation will be. Furthermore ions such as $Na^+$, $K^+$, and $Ca^{2+}$ have been reported to be nontoxic to platinum (J. T. Richardson, "Principles of Catalyst Development," Plenum Press, New York, 1989, p. 206) and in view of the above are considered to be non-toxic toward palladium.

U.S. Pat. No. 2,942,036 claims a process for hydrogenating 1,2,2-trichloropentafluoropropane over a palladium supported on activated carbon catalyst. The carbon support may be treated prior to depositing palladium on it with aqueous HF. The purpose of this treatment is to remove any silica from the carbon.

Various processes using catalysts containing acid-washed carbon have been studied. A. A. Goleva et al., Russ. J. Phys. Chem., $44^2$, 290–1 (1970) disclose the dehydrochlorination of 1,1,2,2-tetrachlorethane to trichloroethylene and HCl using activated charcoal as the catalyst. Activated charcoal treated with hydrochloric acid proved to be more active than an untreated specimen for the production of the olefin, trichloroethylene. M. Biswas et al, J. Macromol. Sci., Chem., A20(8), 861–76 (1983) disclose that the activity of carbon black catalysts for the polymerization of N-vinylcarbazole can be enhanced by treatment with protonic acids such as $HNO_3$, $H_2SO_4$ and $HClO_4$. Chem. Abst. 80 (25): 145470q and Chem. Abst. 80 (25): 145469w disclose an increase in yields of unsaturated glycol diesters when the active carbon catalyst support was treated with $HNO_3$ compared with untreated carbon.

SUMMARY OF THE INVENTION

This invention provides a process for the catalytic hydrogenolysis of fluorohalocarbons and fluorohalohydrocarbons using a catalyst of at least one metal selected from the group consisting of rhenium, cobalt, nickel, ruthenium, rhodium, palladium, osmium, iridium, and platinum supported on carbon, which is characterized by said catalyst containing less than about 200 parts per million (ppm) phosphorus and less than about 200 ppm sulfur based on the total weight of the catalyst. Suitable hydrogenolysis catalysts may be prepared by treating a carbon support with acid, washing said support with deionized water, drying said support, and depositing a catalyst precursor (e.g. palladium chloride) on said support. Preferred catalysts for hydrogenolysis contain less than about 100 ppm potassium.

The process of this invention is considered particularly useful for the conversion of 2,2-dichloro-1,1,1,2-tetrafluoroethane (CFC-114a) to 2-chloro- 1,1,1,2-tetrafluoroethane (HCFC-124) and 1,1,1,2-tetrafluoroethane (HFC-134a), and HCFC-124 to HFC-134a.

DETAILS OF THE INVENTION

This invention provides a process for the catalytic hydrogenolysis of fluorohalocarbons and fluorohalohydrocarbons using a low phosphorus, low sulfur carbon supported catalyst containing at least one metal selected from the group consisting of rhenium, cobalt, nickel, ruthenium, rhodium, palladium, osmium, iridium and platinum. In accordance with this invention, the catalyst used for hydrogenolysis contains less than about 200 ppm phosphorus and less than about 200 ppm sulfur (based on the total catalyst weight).

The fluorohalocarbons and/or fluorohalohydrocarbons used in the hydrogenolysis reactions of this invention are preferably those wherein halo is chloro or bromo. Included are fluorohalocarbons consisting of carbon, fluorine and chlorine and/or bromine; and fluorohalohydrocarbons, consisting of carbon, fluorine, hydrogen, and chlorine and/or bromine. Hydrogenolysis of chlorofluorocarbons (i.e. CFCs) and hydrochlorofluorocarbons, (i.e. HCFCs) is thus provided by this invention. Suitable fluorohalocarbons and fluorohalohydrocarbons may contain 1 to 6 carbon atoms, and include the cyclic as well as acyclic compounds represented by the empirical formula $C_nH_mF_pX_q$, wherein each X is independently selected from Cl and Br, and is preferably Cl, and wherein n is an integer from 1 to 6, m is an integer from 0 to 12, p is an integer from 1 to 13, and q is an integer from 1 to 13, provided that m+p+q equals 2n+2 when the compound is saturated and acyclic, equals 2n when the compound is saturated and cyclic or is olefinic and acyclic, and equals 2n−2 when the compound is olefinic and cyclic. The hydrogenolysis process produces predominantly saturated products.

Preferred applications include hydrogenolysis of compounds containing 1 to 3 carbon atoms. Examples of acyclic compounds which undergo hydrogenolysis include 1,1,1,2-tetrachloro-2,2-difluoroethane (CFC-112a), which may be hydrogenolyzed to 1,1-difluoroethane (HFC-152a); 1,1,2-trichloro-1,2,2-trifluoroethane (CFC-113) which may be hydrogenolyzed to 1,1-dichloro-1,2,2-trifluoroethane (HCFC-123a); 1,1,1-trichloro-2,2,2-trifluoroethane (CFC-113a) which may be hydrogenolyzed to 2,2,-dichloro-1,1,1,-trifluoroethane (HCFC-123); 1,2-dichloro-1,1,2,2-tetrafluoroethane (CFC-114) which may be hydrogenolyzed to 1-chloro-1,1,2,2-tetrafluoroethane (HCFC-124a) and 1,1,2,2,-tetrafluoroethane (HFC-134); 2,2-dichloro-1,1,1,2-tetrafluoroethane (CFC-114a), which may be hydrogenolyzed to 2-chloro-1,1,1,2-tetrafluoroethane (HCFC-124) and 1,1,1,2-tetrafluoroethane (HFC-134a); and HCFC-124 itself which may be hydrogenolyzed to HFC-134a. Examples of cyclic compounds include 4,5-dichloro-1,1,2,2,3,3-hexafluorocyclopentane which may be hydrogenolyzed to 1,1,2,2,3,3-hexafluorocyclopentane.

In a preferred embodiment the fluorohalocarbons and/or fluorhalohydrocarbons are represented by the above empirical formula where n is 1 to 3, m is 0 to 6, p is 1 to 7, and q is 1 to 7.

In accordance with this invention the fluorohalocarbon(s) and/or fluorohalohydrocarbon(s) to be hydrogenolyzed are reacted with hydrogen at an elevated temperature in the presence of the low-phosphorus, low-sulfur carbon supported catalysts disclosed herein. Preferred catalysts for the hydrogenolysis contain less than about 100 ppm potassium. Most preferably the catalysts contain less than about 100 ppm sodium and/or less than about 100 ppm iron.

The reaction is suitably carried out at a temperature which is at least about 125° C. Typically temperatures are about 350° C. or less. Preferred temperatures depend to some extent upon the particular fluorohalocarbon(s) and/or fluorohalohydrocarbon(s) to be reacted.

A conventional amount of $H_2$ is used. Generally, in order to provide substantial hydrogenolysis product yields, the amount of hydrogen used is at least about 0.5 moles per mole of fluorohalocarbon and/or fluorohalohydrocarbon used. To provide yields desired in many embodiments, at least stoichiometric amounts of hydrogen are used. Hydrogen in considerable excess of the stoichiometric amount (e.g. ten times the stoichiometric amount) may be used where rapid hydrogenolysis is desired.

The hydrogenolysis of fluorohalocarbons or fluorohydrohalocarbons can be performed in liquid or vapor-phase using well-known chemical engineering practice, which includes continuous, semi-continuous or batch operations. The hydrogenolysis process is typically achieved at atmospheric or superatmospheric pressures.

In accordance with this invention, supported catalysts suitable for hydrogenolysis are provided which contain at least one metal selected from the group consisting of rhenium, cobalt, nickel, ruthenium, rhodium, palladium, osmium, iridium and platinum. Said metal component is supported on carbon and typically constitutes between about 0.1 and 10 percent by weight of the catalyst.

Suitable catalysts may be prepared by treating the carbon used as catalyst support with acid. Typically the support is then washed with deionized water and dried; and the metal is then deposited thereon using deposit techniques well known in the art (e.g. using a catalyst precursor such as palladium chloride). Preferably the acid used contains neither phosphorus nor sulfur. The carbon is treated with acid such that after such treatment and the subsequent deposit of the metal component, the catalyst contains less than about 200 ppm phosphorus and less than 200 ppm sulfur; preferably less than 100 ppm phosphorus and less than 100 ppm sulfur; and most preferably less than 50 ppm phosphorus and less than 50 ppm sulfur. The preferred catalysts of this invention also contain less than about 100 ppm potassium. Washing the carbon with an acid which provides removal of excess potassium as well as phosphorus and sulfur is thus particularly preferred. Most preferably the catalyst of this invention contain less than about 100 ppm sodium and/or less than about 100 ppm iron. Accordingly, washing with acids that remove excess sodium and iron is especially preferred. Commercially available carbons which may be treated with acid to provide suitable supports include those sold under the following trademarks: Darco™, Nuchar™, Columbia SBV™, Columbia MBV™, Columbia MBQ™, Columbia JXC™, Columbia CXC™, Calgon PCB™, and Barnaby Cheny NB™. The carbon support can be in the form of powder, granules, or pellets, etc.

Examples of acids which may be used in the catalyst preparation process include organic acids such as acetic acid and inorganic acids, e.g., HCl or $HNO_3$. Preferably hydrochloric acid or nitric acid is used. The acid treatment may be accomplished in several ways. A preferred embodiment is described below.

A carbon support is soaked overnight with gentle stirring in a 1 molar solution of the acid prepared in deionized water. The carbon support is then separated and washed at least 10 times with deionized water or until the pH of the washings is about 3. The carbon support is then soaked again with gentle stirring in a 1 molar solution of the acid prepared in deionized water for 12 to 24 hours. The carbon support is then finally washed with deionized water until the washings are substantially free of the anion of the acid (e.g., $Cl^-$ or $NO_3^-$), when tested by standard procedures. The carbon support is separated and dried at 150° C. prior to its use as a support.

Practice of the invention will become further apparent from the following non-limiting examples.

EXAMPLES

Preparation of Acid-Washed Carbon

A commercially available carbon (525 g, 12×30 mesh granules) was soaked overnight with mild stirring in 1M HCl (4 L, prepared in deionized water). The carbon granules were collected on a medium fritted glass funnel and washed 15× with deionized water (2 L each time); final wash pH was 3.10. The carbon granules were soaked again overnight with mild stirring in 1M HCl (4 L, prepared in deionized water). After this treatment, the carbon granules were collected on a fritted glass funnel and washed with deionized water (150 L) until the washings were chloride free when tested with silver nitrate. Finally the carbon granules were dried at 150° C. for 72 h to obtain 452.6 g of dried granules. The ash content and the elements present in the carbon before and after acid washing are shown in Table I.

TABLE I

Elemental Analysis of Carbon Granules

| | AW[a] | NAW[b] |
|---|---|---|
| P | 16 ppm | 333 ppm |
| S | <40 ppm | 378 ppm |
| Si | 800 ppm | 900 ppm |
| Cu | 20 ppm | 21 ppm |
| Mn | 3 ppm | 15 ppm |
| Fe | 60 ppm | 205 ppm |
| Ba | 1 ppm | 13 ppm |
| Ca | 18 ppm | 647 ppm |
| Zn | <5 ppm | <5 ppm |
| K | 77 ppm | 9500 ppm |
| Al | <130 ppm | 290 ppm |
| Na | 39 ppm | 720 ppm |
| Ti | 6 ppm | 11 ppm |
| Ash | 0.25% | 2.19% |

[a] acid-washed (used to prepare Catalyst B)
[b] not acid-washed (used to prepare Catalyst A)

Example 1

Hydrogenolysis of $CF_3CCl_2F$ (CFC-114a)

Eight different 1% Pd/C catalysts were prepared and used to catalyze the hydrogenolysis of CFC-114a to $CF_3CHClF$ (HCFC-124) and $CF_3CH_2F$ (HFC-134a), and the hydrogenolysis of HCFC-124 to HFC-134a. The results of experiments using these eight catalysts are shown in Tables II and III.

Catalyst A

1% Pd on Non-Acid-Washed (NAW) Carbon

Commercial PCB carbon (50 g, 12×30 mesh granules) was added to a solution of palladium chloride (0.84 g) in conc. HCl (3 mL) and deionized water (80 mL). The slurry was stirred occasionally at room temperature for 3 h. It was then dried with frequent stirring at 120° C. for 72 h in air to obtain 51.54 g of 1% Pd on carbon.

Catalyst B

1% Pd on Acid-Washed (AW) Carbon

A sample (200 g) of acid washed carbon prepared as described above was added to a solution of palladium chloride (3.36 g) in conc. hydrochloric acid (12 mL) and deionized water (320 mL). The slurry was stirred occasionally at room temperature for 3 h. It was then dried with frequent stirring at 150° C. for 42 h in air to obtain 205.1 g of 1% Pd on carbon (analysis showed 0.93% Pd).

Catalyst C

Potassium-Doped Palladium on Carbon

A sample (25.0 g) of Catalyst B was added to a solution of potassium chloride (0.46 g) in deionized water (40 mL). The slurry was stirred occasionally at room temperature for 3 h. It was then dried with frequent stirring at 150° C. for 18 h in air to obtain 25.34 g of K-doped (0.95%) 1% Pd on carbon.

Catalyst D

Sodium-Doped Palladium on Carbon

A sample (25.0 g) of Catalyst B was added to a solution of sodium chloride (0.046 g) in deionized water (40 mL). The slurry was stirred occasionally at room temperature for 3 h. It was then dried with frequent stirring at 150° C. for 18 h in air to obtain 24.94 g of Na-doped (720 ppm) 1% Pd on carbon.

Catalyst E

Calcium-Doped Palladium on Carbon

A sample (25.0 g) of Catalyst B was added to a solution of calcium chloride (0.045 g) in deionized water (40 mL). The slurry was stirred occasionally at room temperature for 3 h. It was then dried with frequent stirring at 150° C. for 18 h in air to obtain 24.99 g of Ca-doped (650 ppm) 1% Pd on carbon.

Catalyst F

Phosphorus-Doped Palladium on Carbon

A sample (25.0 g) of Catalyst B was added to a solution of $K_2HPO_4$ (0.046 g) in deionized water (40 mL). The slurry was stirred occasionally at room temperature for 3 h. It was then dried with frequent stirring at 150° C. for 18 h in air to obtain 24.98 g of P-doped (320 ppm) 1% Pd on carbon.

Catalyst G

Sulfur-Doped Palladium on Carbon

A sample (25.0 g) of Catalyst B was added to a solution of potassium sulfate (0.052 g) in deionized water (40 mL). The slurry was stirred occasionally at room temperature for 3 h. It was then dried with frequent stirring at 150° C. for 18 h in air to obtain 25.00 g of S-doped (370 ppm) 1% Pd on carbon.

Catalyst H

Iron-Doped Palladium on Carbon

A sample (25.0 g) of Catalyst B was added to a solution of ferric chloride (0.015 g) in deionized water (40 mL). The slurry was stirred occasionally at room temperature for 3 h. It was then dried with frequent stirring at 150° C. for 18 h in air to obtain 24.94 g of Fe-doped (200 ppm) 1% Pd on carbon.

General Procedure for Catalyst Evaluation

A 6"×½" O.D. Hastelloy™ C nickel alloy reactor was charged with the catalyst (5.0 g) for evaluation. The reactor contents were heated to a temperature of 175° C. over a period of five hours, during which time an equimolar flow, 10 cc/min each, of nitrogen and hydrogen was passed through the reactor. At the end of this five hour period, nitrogen flow was stopped, the hydrogen flow increased to 20 mL/min, the reactor temperature raised to 275° C. over a 2½ hour period and maintained at this temperature for an additional 16 hours. After this period, the reactor temperature was decreased to the desired operating temperature for catalyst evaluation.

General Procedure for Product Analysis

The products leaving the reactor were analyzed on line using a gas chromatograph. The column consisted of a 20'×⅛" s/s tube containing Krytox™ perfluorinated polyether on an inert support. Helium was used as the carrier gas. The product analyses are reported in area percent.

The CFC-114a hydrogenolysis was done under the following conditions: temperature—150° C., pressure— atmospheric, $[H_2]/[CFC-114]=2$, total flow=30 cc/min. and the results are shown in Table II. The HCFC-124 hydrogenolysis was done under the following conditions: temperature—250° C., pressure—atmospheric, $[H_2]/[HCFC-124]=1$, total flow=20 cc/min. and the results are shown in Table III.

TABLE II $CF_3CCl_2F \rightarrow CF_3CHClF + CF_3CH_2F$

| Cat. Prep. | % 114a[a] Conv. | % Sel. to 124[b] | % Sel. to 134a[c] | % Sel. to 124 + 134a |
|---|---|---|---|---|
| A (NAW) | 25.6 | 40.3 | 52.5 | 92.8 |
| B (AW) | 65.4 | 10.9 | 85.4 | 97.6 |
| C (K) | 40.2 | 26.7 | 63.3 | 89.9 |
| D (Na) | 49.8 | 12.7 | 83.4 | 96.1 |
| E (Ca) | 58.9 | 14.1 | 82.5 | 96.6 |
| F (P) | 32.3 | 29.2 | 61.8 | 91.0 |
| G (S) | 32.4 | 28.0 | 64.9 | 92.9 |
| H (Fe) | 60.8 | 12.3 | 81.8 | 94.1 |

[a] 114a = CFC – 114a = $CF_3CCl_2F$
[b] 124 = HCFC – 124 = $CF_3CHClF$
[c] 134a = HFC – 134a = $CF_3CH_2F$

Examination of the results in Table II shows that conversion is increased relative to Catalyst Preparation A using catalysts low in both phosphorus and sulfur, and that both conversion (Conv.) and selectivity (Sel.) are increased using Catalyst Preparation B.

TABLE III $CF_3CHClF \rightarrow CF_3CH_2F$

| Cat. Prep. | % 124 Conv. | % Sel. 134a |
|---|---|---|
| A (NAW) | 39.1 | 90.4 |
| B (AW) | 69.0 | 94.0 |
| C (K) | 56.2 | 93.6 |
| D (Na) | 52.0 | 93.6 |
| E (Ca) | 58.3 | 94.3 |
| F (P) | 38.4 | 89.5 |
| G (S) | 40.8 | 93.2 |
| H (Fe) | 57.0 | 92.3 |

Examination of the results in Table III shows that both conversion and selectivity are increased relative to Catalyst Preparation A using catalysts low in both phosphorus and sulfur, especially Catalyst Preparation B.

Particular embodiments of the invention are included in the Examples. Other embodiments will become apparent to those skilled in the art from a consideration of the specification or practice of the invention. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the claims.

What is claimed is:

1. A process for the catalytic hydrogenolysis of a cyclic or acyclic compound having the formula $C_nH_mF_pX_q$ wherein n is an integer from 1 to 6, m is an integer from 0 to 12, p is an integer from 1 to 13, q is an integer from 1 to 13 and each X is independently selected from Cl and Br, provided that m+p+q equals 2n+2 when the compound is saturated and acyclic, equals 2n when the compound is saturated and cyclic or is olefinic and acyclic, and equals 2n−2 when the compound is olefinic and cyclic, using a catalyst of at least one metal selected from the group consisting of rhenium, cobalt, nickel, ruthenium, rhodium, palladium, osmium, iridium and platinum supported on carbon which is characterized by said catalyst containing less than about 200 ppm phosphorus and less than about 200 ppm sulfur.

2. The process of claim 1 wherein the carbon support is acid washed.

3. The process of claim 1 wherein the carbon support is acid washed with acid containing neither phosphorus nor sulfur.

4. The process of claim 1 wherein the carbon support is acid washed with HCl or $HNO_3$.

5. The process of claim 1 wherein each X is Cl.

6. The process of claim 5 wherein the catalyst contains less than 100 ppm potassium.

7. The process of claim 6 wherein the catalyst contains less than 100 ppm sodium.

8. The process of claim 7 wherein the catalyst contains less than 100 ppm iron.

9. The process of claim 1 wherein n is 1 to 3, m is 0 to 6, p is 1 to 7 and q is 1 to 7.

10. The process of claim 1 wherein said at least one metal constitutes between about 0.1 and 10 percent by weight of the catalyst.

11. The process of claim 1 wherein hydrogenolysis is carried out at a temperature between about 125° C. and about 350° C.

12. The process of claim 1 wherein 2,2-dichloro-1,1,1,2-tetrafluoroethane is converted to 2-chloro-1,1,1,2-tetrafluoroethane and 1,1,1,2-tetrafluoroethane.

13. The process of claim 1 wherein 2-chloro-1,1,1,2-tetrafluoroethane is converted to 1,1,1,2-tetrafluoroethane.

14. The process of claim 1 wherein the at least one metal is palladium.

15. The process of claim 1 wherein the at least one metal is ruthenium.

16. The process of claim 10 wherein the at least one metal is palladium.

17. The process of claim 12 wherein the at least one metal is palladium.

18. The process of claim 1 wherein the at least one metal is nickel.

19. A process for the catalytic hydrogenolysis of 4,5-dichloro-1,1,2,2,3,3-hexafluorocyclopentane to form 1,1,2,2,3,3-hexafluorocyclopentane, characterized by using a catalyst of rhenium supported on carbon; said catalyst containing less than about 200 ppm phosphorus and less than about 200 ppm sulfur.

20. A process for the catalytic hydrogenolysis of a cyclic or acyclic compound having the formula $C_nH_mF_pX_q$ wherein n is an integer from 1 to 6, m is an integer from 0 to 12, p is an integer from 1 to 13, q is an integer from 1 to 13 and each X is independently selected from Cl and Br, provided that m+p+q equals 2n+2 when the compound is saturated and acyclic equals 2n when the compound is saturated and cyclic or is olefinic and acyclic, and equals 2n−2 when the compound is olefinic and cyclic, using a catalyst of at least one metal selected from the group consisting of rhenium, cobalt, nickel, ruthenium, rhodium, palladium, osmium, iridium and platinum supported on carbon characterized by: (1) treating the carbon with acid; and (2) subsequently depositing said metal thereon; said treatment of the carbon with acid being such that after said deposit of metal, the catalyst employed for said hydrogenolysis contains between about 0.1 and 10 percent by weight of said metal, less than about 200 ppm phosphorus and less than about 200 ppm sulfur.

* * * * *